(12) United States Patent
Young

(10) Patent No.: US 8,945,231 B2
(45) Date of Patent: Feb. 3, 2015

(54) COMPOSITE TRIAL PROSTHESIS

(75) Inventor: Duncan Young, Beeston (GB)

(73) Assignee: Depuy (Ireland), Cork (IE)

( * ) Notice: Subject to any disclaimer, the term of this patent is extended or adjusted under 35 U.S.C. 154(b) by 31 days.

(21) Appl. No.: 13/642,560

(22) PCT Filed: Mar. 23, 2011

(86) PCT No.: PCT/GB2011/050574
§ 371 (c)(1),
(2), (4) Date: Jan. 9, 2013

(87) PCT Pub. No.: WO2011/131957
PCT Pub. Date: Oct. 27, 2011

(65) Prior Publication Data
US 2013/0103160 A1  Apr. 25, 2013

(30) Foreign Application Priority Data

Apr. 22, 2010 (GB) .................................. 1006716.3

(51) Int. Cl.
A61F 2/38 (2006.01)
A61F 2/46 (2006.01)
A61F 2/30 (2006.01)

(52) U.S. Cl.
CPC ............... A61F 2/389 (2013.01); A61F 2/4684 (2013.01); A61F 2002/30616 (2013.01); A61F 2002/4661 (2013.01)
USPC .................................................... 623/20.32

(58) Field of Classification Search
CPC  A61F 2/4684; A61F 2/389; A61F 2002/4661
USPC .......... 623/20.14–20.36, 21.11–21.19, 22.11, 623/22.21, 22.4, 17.11–17.14
See application file for complete search history.

(56) References Cited

U.S. PATENT DOCUMENTS

| 4,135,517 A | * | 1/1979 | Reale ........................... 606/86 R |
| 4,211,228 A | * | 7/1980 | Cloutier ........................ 606/102 |
| 4,378,607 A | * | 4/1983 | Wadsworth ................ 623/20.11 |
| 4,938,769 A | * | 7/1990 | Shaw ......................... 623/20.15 |
| 4,944,757 A | * | 7/1990 | Martinez et al. ........... 623/20.15 |
| 5,019,103 A | * | 5/1991 | Van Zile et al. ............ 623/20.34 |
| 5,047,058 A | * | 9/1991 | Roberts et al. ............. 623/20.16 |
| 5,152,797 A | * | 10/1992 | Luckman et al. .......... 623/20.16 |
| 5,197,488 A | * | 3/1993 | Kovacevic ..................... 600/595 |
| 5,344,458 A | * | 9/1994 | Bonutti ...................... 623/20.32 |
| 5,387,241 A | * | 2/1995 | Hayes ........................ 623/20.16 |
| 5,464,406 A | * | 11/1995 | Ritter et al. ................. 606/86 R |
| 5,470,354 A | * | 11/1995 | Hershberger et al. ......... 128/898 |

(Continued)

FOREIGN PATENT DOCUMENTS

WO    WO 9709939 A1    3/1997
WO    WO 2008024836 A2    2/2008

OTHER PUBLICATIONS

PCT International Search Report and Written Opinion PCT/GB2011/050574 dated Jun. 17, 2011.

(Continued)

Primary Examiner — Alvin Stewart

(57) ABSTRACT

A composite trial prosthesis comprises a first component (2) and a shim (4). The first component (2) has a first surface (8) corresponding to a surface of a prosthetic component and a reverse surface (10). The shim (4) is arranged to couple to the reverse surface (10). The first component (2) further comprises a first marking (24) which is arranged to be visible when the first component (2) is coupled directly to a bone or a further prosthetic component. Part of the shim (26) is arranged to obscure the first marking (24) when the shim (4) is coupled to the reverse surface (10), the shim (4) further comprising a second marking (28) which is visible when the shim (4) is coupled to a bone or a further prosthetic component. A set of composite trial prostheses and a method of selecting a required surgical prosthesis are also disclosed.

14 Claims, 2 Drawing Sheets

(56) References Cited

U.S. PATENT DOCUMENTS

| | | | | |
|---|---|---|---|---|
| 5,472,415 A * | 12/1995 | King et al. | 606/102 |
| 5,569,263 A * | 10/1996 | Hein | 606/102 |
| 5,607,431 A * | 3/1997 | Dudasik et al. | 606/80 |
| 5,613,970 A * | 3/1997 | Houston et al. | 606/88 |
| 5,683,469 A | 11/1997 | Johnson et al. | |
| 5,702,464 A * | 12/1997 | Lackey et al. | 623/20.32 |
| 5,716,361 A * | 2/1998 | Masini | 606/86 R |
| 5,733,292 A * | 3/1998 | Gustilo et al. | 606/88 |
| 5,766,261 A * | 6/1998 | Neal et al. | 623/21.15 |
| 5,776,200 A * | 7/1998 | Johnson et al. | 623/20.15 |
| 5,776,201 A * | 7/1998 | Colleran et al. | 623/20.15 |
| 5,782,925 A * | 7/1998 | Collazo et al. | 623/20.28 |
| 5,792,143 A * | 8/1998 | Samuelson et al. | 606/102 |
| 5,860,969 A * | 1/1999 | White et al. | 623/23.35 |
| 5,860,982 A * | 1/1999 | Ro et al. | 606/102 |
| 5,928,286 A * | 7/1999 | Ashby et al. | 623/20.33 |
| 5,941,884 A * | 8/1999 | Corvelli et al. | 606/88 |
| 5,976,147 A | 11/1999 | LaSalle et al. | |
| 5,989,261 A * | 11/1999 | Walker et al. | 606/102 |
| 6,080,196 A * | 6/2000 | Bertin | 623/20.14 |
| 6,102,953 A * | 8/2000 | Huebner | 623/19.11 |
| 6,106,529 A * | 8/2000 | Techiera | 606/88 |
| 6,193,758 B1 * | 2/2001 | Huebner | 623/19.14 |
| 6,214,052 B1 * | 4/2001 | Burkinshaw | 623/20.34 |
| 6,277,123 B1 * | 8/2001 | Maroney et al. | 606/102 |
| 6,641,614 B1 * | 11/2003 | Wagner et al. | 623/17.15 |
| 6,673,114 B2 * | 1/2004 | Hartdegen et al. | 623/19.12 |
| 6,702,824 B2 * | 3/2004 | Maroney et al. | 606/99 |
| 6,723,097 B2 * | 4/2004 | Fraser et al. | 606/86 A |
| 6,736,852 B2 * | 5/2004 | Callaway et al. | 623/19.14 |
| 6,743,258 B1 * | 6/2004 | Keller | 623/20.14 |
| 6,746,487 B2 * | 6/2004 | Scifert et al. | 623/22.12 |
| 6,827,723 B2 * | 12/2004 | Carson | 606/130 |
| 6,827,739 B2 * | 12/2004 | Griner et al. | 623/16.11 |
| 6,916,324 B2 * | 7/2005 | Sanford et al. | 606/87 |
| 6,923,817 B2 * | 8/2005 | Carson et al. | 606/130 |
| 7,105,026 B2 * | 9/2006 | Johnson et al. | 623/20.14 |
| 7,135,044 B2 * | 11/2006 | Bassik et al. | 623/22.42 |
| 7,141,067 B2 * | 11/2006 | Jones et al. | 623/16.11 |
| 7,247,169 B1 * | 7/2007 | Lo et al. | 623/17.11 |
| 7,309,363 B2 * | 12/2007 | Dietz | 623/23.47 |
| 7,338,496 B1 * | 3/2008 | Winslow et al. | 606/87 |
| 7,338,499 B1 * | 3/2008 | Kuczynski et al. | 606/102 |
| 7,435,263 B2 * | 10/2008 | Barnett et al. | 623/19.12 |
| 7,632,283 B2 * | 12/2009 | Heldreth | 606/102 |
| 7,632,314 B2 * | 12/2009 | Dietz | 623/20.33 |
| 7,634,306 B2 * | 12/2009 | Sarin et al. | 600/426 |
| 7,686,812 B2 * | 3/2010 | Axelson et al. | 606/88 |
| 7,691,150 B2 * | 4/2010 | Cronin et al. | 623/20.32 |
| 7,699,853 B2 * | 4/2010 | Durand-Allen et al. | 606/99 |
| 7,837,690 B2 * | 11/2010 | Metzger | 606/87 |
| 7,854,737 B2 * | 12/2010 | Daniels et al. | 606/102 |
| 7,959,635 B1 * | 6/2011 | Bonutti | 606/82 |
| 7,963,969 B2 * | 6/2011 | Sanford | 606/88 |
| 8,012,215 B2 * | 9/2011 | Metzger et al. | 623/20.15 |
| 8,029,574 B2 * | 10/2011 | Kellar et al. | 623/23.41 |
| 8,052,758 B1 * | 11/2011 | Winslow | 623/22.42 |
| 8,065,927 B2 * | 11/2011 | Crottet et al. | 73/862.627 |
| 8,066,777 B2 * | 11/2011 | Palmer et al. | 623/21.14 |
| 8,070,752 B2 * | 12/2011 | Metzger et al. | 606/88 |
| 8,070,823 B2 * | 12/2011 | Kellar et al. | 623/23.4 |
| 8,092,545 B2 * | 1/2012 | Coon et al. | 623/20.32 |
| 8,109,942 B2 * | 2/2012 | Carson | 606/130 |
| 8,128,705 B2 * | 3/2012 | Birkbeck et al. | 623/23.11 |
| 8,133,282 B2 * | 3/2012 | Hushka et al. | 623/17.16 |
| 8,137,358 B2 * | 3/2012 | Winslow et al. | 606/87 |
| 8,141,437 B2 * | 3/2012 | Amirouche et al. | 73/862.041 |
| 8,142,512 B2 * | 3/2012 | Brooks et al. | 623/23.4 |
| 8,187,283 B2 * | 5/2012 | Thomas | 606/102 |
| 8,197,489 B2 * | 6/2012 | Chessar et al. | 606/90 |
| 8,197,549 B2 * | 6/2012 | Amirouche et al. | 623/20.29 |
| 8,231,631 B2 * | 7/2012 | Lavallee et al. | 606/90 |
| 8,357,166 B2 * | 1/2013 | Aram et al. | 606/88 |
| 8,414,653 B2 * | 4/2013 | Burstein et al. | 623/20.32 |
| 8,419,740 B2 * | 4/2013 | Aram et al. | 606/88 |
| 8,425,615 B2 * | 4/2013 | Berelsman et al. | 623/20.11 |
| 8,435,304 B2 * | 5/2013 | Dietz | 623/20.32 |
| 8,480,677 B2 * | 7/2013 | Groh | 606/86 R |
| 8,491,589 B2 * | 7/2013 | Fisher et al. | 606/88 |
| 8,491,664 B2 * | 7/2013 | McMahon et al. | 623/22.11 |
| 8,498,711 B2 * | 7/2013 | Roche | 607/46 |
| 8,506,571 B2 * | 8/2013 | Chana et al. | 606/88 |
| 8,529,578 B2 * | 9/2013 | Daniels et al. | 606/102 |
| 8,535,382 B2 * | 9/2013 | Kehres et al. | 623/20.11 |
| 8,568,485 B2 * | 10/2013 | Ries et al. | 623/20.29 |
| 8,585,710 B2 * | 11/2013 | Fischer et al. | 606/102 |
| 8,585,711 B2 * | 11/2013 | Klotz et al. | 606/102 |
| 8,591,593 B2 * | 11/2013 | Metzger | 623/20.32 |
| 8,597,358 B2 * | 12/2013 | Landry et al. | 623/17.15 |
| 8,603,101 B2 * | 12/2013 | Claypool et al. | 606/102 |
| 8,617,250 B2 * | 12/2013 | Metzger | 623/20.32 |
| 2001/0053935 A1 * | 12/2001 | Hartdegen et al. | 623/19.12 |
| 2004/0097951 A1 | 5/2004 | Steffensmeier | |
| 2006/0069447 A1 * | 3/2006 | DiSilvestro et al. | 623/23.16 |
| 2006/0111790 A1 | 5/2006 | Dietz | |
| 2006/0184176 A1 | 8/2006 | Straszheim-Morley et al. | |
| 2007/0239165 A1 | 10/2007 | Amirouche | |
| 2009/0084491 A1 * | 4/2009 | Uthgenannt et al. | 156/153 |
| 2009/0216325 A1 * | 8/2009 | May et al. | 623/11.11 |
| 2009/0265013 A1 * | 10/2009 | Mandell | 623/20.21 |
| 2010/0010635 A1 * | 1/2010 | Straszheim-Morley et al. | 623/20.32 |
| 2010/0298941 A1 | 11/2010 | Hes et al. | |
| 2011/0066246 A1 | 3/2011 | Ries et al. | |
| 2012/0158152 A1 * | 6/2012 | Claypool et al. | 623/20.33 |
| 2012/0209391 A1 * | 8/2012 | Cipolletti et al. | 623/18.11 |
| 2012/0226481 A1 * | 9/2012 | Carson | 703/1 |
| 2012/0239160 A1 * | 9/2012 | Belew et al. | 623/20.35 |
| 2012/0259339 A1 * | 10/2012 | Hood et al. | 606/80 |
| 2012/0259421 A1 * | 10/2012 | Satterthwaite et al. | 623/22.42 |
| 2012/0265317 A1 * | 10/2012 | Metzger | 623/20.33 |
| 2013/0006252 A1 * | 1/2013 | Waite et al. | 606/88 |
| 2013/0006376 A1 * | 1/2013 | Wogoman et al. | 623/20.32 |
| 2013/0006377 A1 * | 1/2013 | Waite et al. | 623/20.32 |
| 2013/0013075 A1 * | 1/2013 | Fisher et al. | 623/20.15 |
| 2013/0020733 A1 * | 1/2013 | Berger | 264/40.1 |
| 2013/0024001 A1 * | 1/2013 | Wentorf et al. | 623/20.32 |
| 2013/0030538 A1 * | 1/2013 | Metzger et al. | 623/20.3 |
| 2013/0046385 A1 * | 2/2013 | Hartdegen et al. | 623/20.34 |
| 2013/0079671 A1 * | 3/2013 | Stein et al. | 600/587 |
| 2013/0096567 A1 * | 4/2013 | Fisher et al. | 606/102 |
| 2013/0103153 A1 * | 4/2013 | Blackwell et al. | 623/17.16 |
| 2013/0103160 A1 * | 4/2013 | Young | 623/20.32 |
| 2013/0173011 A1 * | 7/2013 | Otto et al. | 623/20.32 |
| 2013/0184834 A1 * | 7/2013 | Brooks et al. | 623/23.42 |
| 2013/0190885 A1 * | 7/2013 | Ammann et al. | 623/20.32 |
| 2013/0204267 A1 * | 8/2013 | Dietz | 606/102 |
| 2013/0204377 A1 * | 8/2013 | Samuelson et al. | 623/20.15 |
| 2013/0211531 A1 * | 8/2013 | Steines et al. | 623/20.35 |
| 2013/0245769 A1 * | 9/2013 | Gimbel et al. | 623/17.16 |
| 2013/0245803 A1 * | 9/2013 | Lang | 700/98 |
| 2013/0261505 A1 * | 10/2013 | Sherman et al. | 600/595 |
| 2013/0261758 A1 * | 10/2013 | Claypool et al. | 623/20.32 |
| 2013/0261759 A1 * | 10/2013 | Claypool et al. | 623/20.33 |
| 2013/0282132 A1 * | 10/2013 | White et al. | 623/20.21 |
| 2013/0289569 A1 * | 10/2013 | Wilkinson | 606/88 |
| 2013/0289726 A1 * | 10/2013 | Curran et al. | 623/17.16 |
| 2013/0304221 A1 * | 11/2013 | Blaylock et al. | 623/20.32 |
| 2014/0039636 A1 * | 2/2014 | Kurtz | 623/20.32 |
| 2014/0052269 A1 * | 2/2014 | Claypool et al. | 623/20.33 |
| 2014/0081412 A1 * | 3/2014 | Metzger | 623/20.33 |
| 2014/0155902 A1 * | 6/2014 | Sikora et al. | 606/88 |
| 2014/0156017 A1 * | 6/2014 | Salyer | 623/20.34 |
| 2014/0159282 A1 * | 6/2014 | Smith et al. | 264/328.7 |
| 2014/0172112 A1 * | 6/2014 | Marter | 623/20.32 |

OTHER PUBLICATIONS

UK Search Report GB1006716.3 dated Aug. 10, 2010.

* cited by examiner

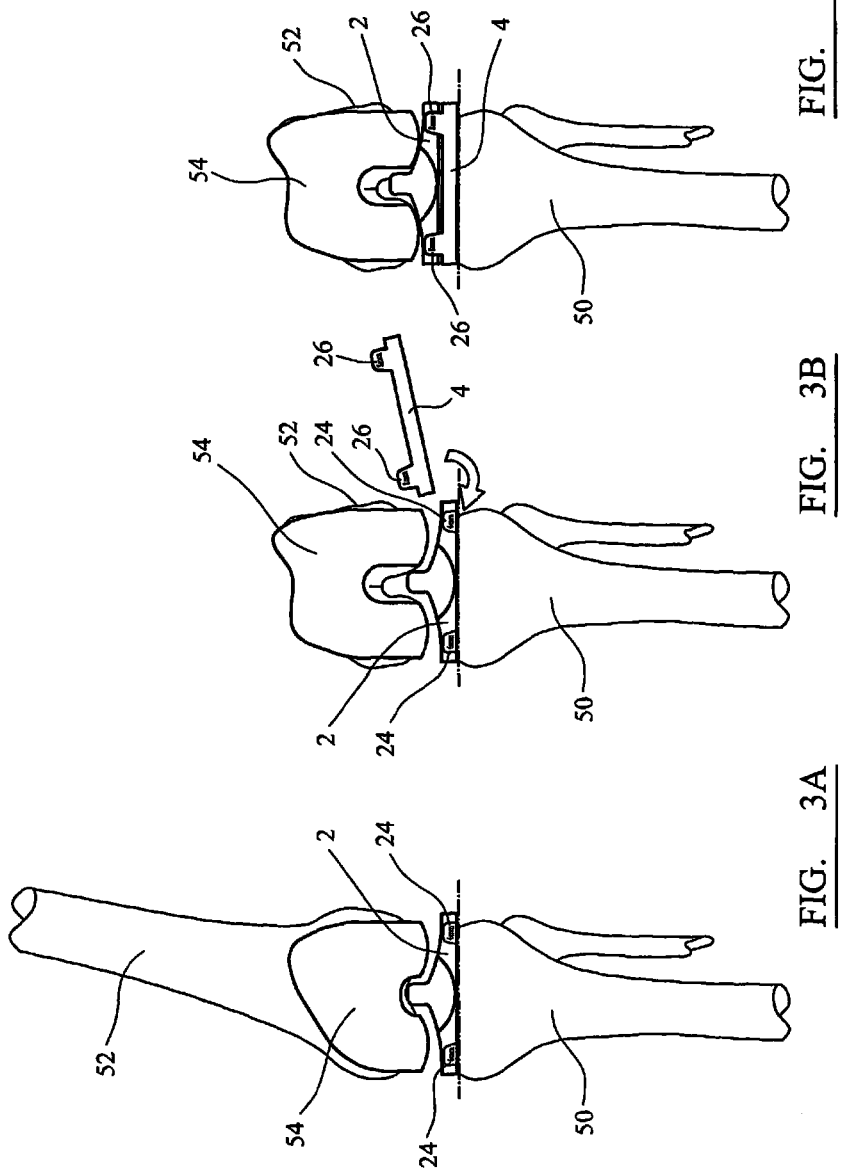

COMPOSITE TRIAL PROSTHESIS

CROSS REFERENCE TO RELATED APPLICATION

This application is a National Stage 35 U.S.C. 371 of International Patent Application PCT/GB2011/050574 filed Mar. 23, 2011.

BACKGROUND OF THE INVENTION

The present invention relates to a composite trial prosthesis. In particular, embodiments of the present invention relate to a composite trial tibial insert for coupling between a trial tibial tray and a trial femoral component during a knee replacement procedure. The present invention also relates to methods of using composite trial prostheses.

During the lifetime of a patient, it may be necessary to perform a joint replacement procedure on the patient as a result of, for example, disease or trauma. The joint replacement procedure, or joint arthroplasty, may involve the use of a prosthesis which is implanted into one or more of the patient's bones. For instance, during a knee replacement procedure a femoral prosthesis is implanted at the distal end of the femur and a tibial tray prosthesis is implanted at the proximal end of the tibia. Coupled between the two is a tibial insert to adjust the gap between the femoral and tibial prostheses to maintain correct soft tissue tension surrounding the knee. The tibial inserts are available in a range of thicknesses to accommodate different joint spaces between the femur and the tibia and to provide different bearing surfaces to correspond to the selected size and shape of the femoral prosthesis.

A surgical instrument set for performing a knee replacement procedure is marketed by DePuy Orthopaedics, Inc. under the trade mark Sigma High Performance Instruments. The initial surgical steps comprise resecting and shaping the distal end of the femur and the proximal end of the tibia to receive the femoral and tibial prostheses. Trial femoral and tibial prostheses are then temporarily implanted and a trial tibial insert that matches the chosen femoral style and size is inserted and coupled to the trial tibial tray. The joint is then reduced and the knee extended and flexed to assess the stability and alignment of the trial prostheses. It there is instability in the joint then the trial tibial insert is removed and replaced with a trial tibial insert with the same shape bearing, but increased thickness. It will be appreciated that this necessarily requires the Sigma HP instrument set to comprise a large number of trial tibial inserts. Specifically, for every size and style of bearing surface there must be a full range of different thicknesses to accommodate every possible combination.

It is known to provide a smaller range of composite trial tibial inserts in which there is a full range of trial tibial insert bearing components for every required size and shape of femoral prosthesis for the minimum required thickness and a range of standard shaped shims to couple to the bearing components to increase the thickness. However, it will be appreciated that careful marking of the bearing components and the shims is required to prevent the composite thickness of the bearing component plus the shim being incorrectly recorded. Specifically, as the bearing components may be used without shims they must be marked with the minimum thickness they represent (together with information regarding the shape and size of the associated femoral prosthesis). Each shim must also indicate its thickness, or the composite thickness when coupled to the bearing component. If both markings are visible then there is a risk that the marking for the thickness without the shim may be incorrectly recorded as the combined thickness. Furthermore, the shims typically comprise relatively thin sheets that are sandwiched between the bearing component and the trial tibial tray. There may be no other position to mark the shim thickness than on the face of the shim. Consequently, it may not be possible to determine the thickness of the shim without disassembling the bearing component, shim and trial tibial tray. It may be particularly difficult to see the shim markings from the anterior of the joint when the knee joint is reduced.

BRIEF SUMMARY OF THE INVENTION

It is an object of embodiments of the present invention to obviate or mitigate one or more of the problems associated with the prior art, whether identified herein or elsewhere.

According to a first aspect of the present invention there is provided a composite trial prosthesis comprising: a first component having a first surface corresponding to a surface of a prosthetic component and a reverse surface; and a shim arranged to couple to the reverse surface; wherein the first component further comprises a first marking which is arranged to be visible when the first component is coupled directly to a bone or a further prosthetic component; and wherein part of the shim is arranged to obscure the first marking when the shim is coupled to the reverse surface, the shim further comprising a second marking which is visible when the shim is coupled to a bone or a further prosthetic component.

An advantage of the present invention is that because markings on the first component are obscured when the shim is attached the chance of incorrectly recording the wrong information is reduced.

The second marking may be arranged to be visible when the shim is coupled between the first component and a bone or a further prosthetic component.

The first marking may be indicative of the thickness of the first component and the second marking is indicative of the thickness of the composite trial prosthesis or a property of shim.

The shim may further comprise a tab arranged to extend over the first component when the shim is coupled to the reverse surface of the first component to obscure the first marking.

The first component may further comprise a recess and the first marking is at least partially located within the recess, the shim tab being arranged to extend into the recess to obscure the first marking.

The second marking may be at least partially located on the tab.

The tab may further comprise a window allowing at least part of the first component to be visible through the window when the shim is coupled to the reverse surface of the first component.

The shim may comprise at least two tabs and the first component comprises at least two markings, each tab being arranged to obscure a marking.

The first surface may comprise a bearing surface which corresponds to a bearing surface of the prosthetic component.

The composite trial prosthesis may comprise a trial tibial prosthesis and is arranged to couple to a trial tibial tray.

The markings may be visible at one or more of an anterior-medial and an anterior-lateral position when the trial tibial prosthesis is inserted into a knee joint.

According to a second aspect of the present invention there is provided a set of composite trial prostheses comprising: a composite trial prosthesis according to any one of the preceding claims; and at least one further shim arranged to couple to the reverse surface of the first component, each shim having a different thickness to the other shims or a different shape to the other shims.

The set of composite trial prostheses may further comprise at least one further first component arranged to couple to each shim, each first component having a different shape first surface.

According to a third aspect of the present invention there is provided a method of selecting a required surgical prosthesis, the method comprising: coupling a reverse surface of a first component to a bone or a further prosthetic component, the first component having a first surface corresponding to a surface of a prosthetic component; determining whether the first component on its own is a required size and shape when coupled to the bone or further prosthetic component and if so selecting a required size of surgical prosthesis according to data provided by a marking on the first component which remains visible when the first component is coupled to the bone or further prosthetic component; coupling a shim between the reverse surface of the first component and the bone or further prosthetic component to form a composite trial prosthesis if the determination is that the first component on its own is not the required size and shape; and determining whether composite trial prosthesis is the required size and shape when coupled to the bone or further prosthetic component and if so selecting a required size of surgical prosthesis according to data provided by a marking on the shim which remains visible when the composite trial prosthesis is coupled to the bone or further prosthetic component and obscures the marking on the first component.

BRIEF DESCRIPTION OF THE DRAWINGS

Embodiments of the present invention will now be described, by way of example only, with reference to the accompany drawings, in which:

FIGS. 3A to 3C illustrate the process of selecting a required surgical prosthesis using the bearing component and shim of FIGS. 1 and 2.

DETAILED DESCRIPTION OF THE INVENTION

Figure 1:
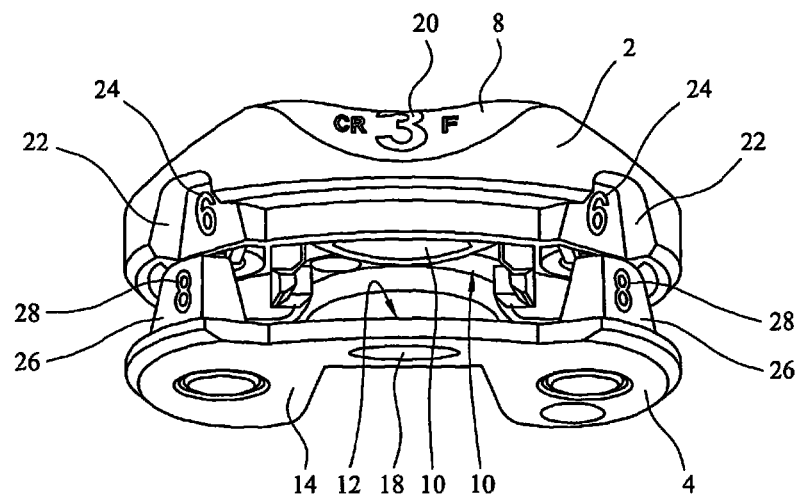
FIG. 1 illustrates an exploded view of a bearing component and a shim.
Figure 2:
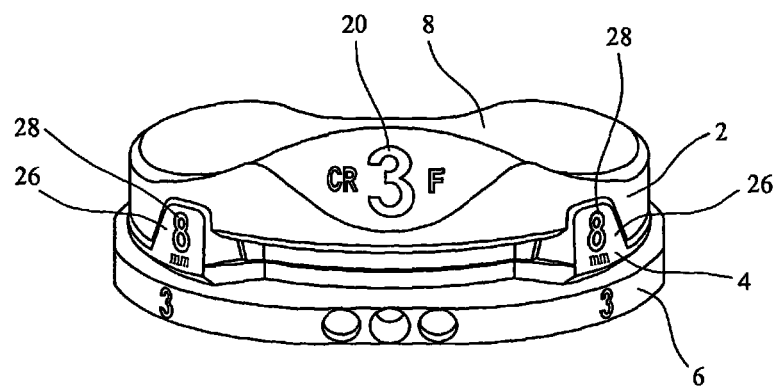
FIG. 2 illustrates the bearing component and the tibial shim coupled together and attached to a trial tibial tray.

Referring to FIGS. 1 and 2 these illustrate a composite trial tibial insert comprising a bearing component 2 and a shim 4. In FIG. 2 the composite trial tibial insert is coupled to a trial tibial tray 6. The bearing component 2 comprises an upper bearing surface 8 which is shaped to fit the trial femoral prosthesis (and corresponds to the bearing surface of the selected tibial insert). The bearing component 4 has a reverse surface 10 which is shaped to receive the shim 4 or to couple directly to a trial tibial tray 6. The reverse surface 10 may comprise a clip to positively couple to the shim 4. The shim 4 has an upper coupling surface 12 to couple to the reverse surface 10 of the bearing component 2 and a lower surface 14 to couple to the trial tibial tray 6. The bearing component reverse surface 10 and the lower surface of the shim 14 are generally similar and include the same coupling portions to connect to the trial tibial tray 6. Specifically, both comprise a bore 16, 18 to couple to a post on the trial tibial tray 6 (not visible in FIG. 2).

The bearing component 2 has markings 20 on the anterior face of the bearing surface 8 indicating the size and shape of the corresponding femoral trial. The bearing component 2 further comprises recesses 22 anterior-laterally and anterior-medially. The back of the recesses display markings 24 indicating the thickness of the bearing component 2 when used on its own. When the bearing component 2 is coupled directly to the trial tibial tray 6 the markings 24 are visible in the reduced knee joint. The shim 4 further comprises upwardly extending tabs 26 at anterior-lateral and anterior-medial parts of the outer edge of the shim 4. The tabs 26 are arranged to be received in the first component recesses 22 when the shim 4 is coupled to the bearing component 2. The tabs 26 have markings 28 indicating the composite thickness of the trial tibial insert when the shim 4 is coupled to the bearing component 2. Furthermore, the tabs 26 obscure the markings 24 at the back of the recesses 22 reducing the risk of incorrectly recording the chosen thickness of tibial insert.

A method of selecting a required size of surgical prosthesis using composite trial prosthesis in accordance with embodiments of the present invention will now be briefly described in connection with FIGS. 3A to 3C. After the knee joint has been prepared the trial tibial and femoral prostheses are coupled to the tibia 50 and femur 52 respectively. The trial femoral prosthesis 54 is visible at the distal end of the femur 52 in FIGS. 3A to 3C, whereas the trial tibial prosthesis is obscured by the bearing component 2 and shim 4. The bearing component 2 can then be coupled directly to the trial tibial prosthesis at the proximal end of the tibia 50 as illustrated in FIG. 3A. The joint may then be reduced and tension within the joint and the biomechanical functioning of the joint assessed. FIG. 3A illustrates an anterior view of the knee in extension. The bearing component 2 on its own corresponds to a tibial insert which is 6 mm thick. It can be seen that in FIG. 3A there is laxity in the knee joint and therefore the bearing component 2 on its own does not correspond to the required size and shape of tibial insert. FIG. 3B illustrates an anterior view of the knee in flexion with the bearing component 2 positioned between the tibia 50 and femur 52. Again it can be seen that there is laxity in the joint, which may be addressed by providing a further 2 mm of distraction by introducing the 8 mm shim (illustrated as sliding under the bearing component 2, but in practice the bearing component 2 may be removed from the joint first). FIG. 3C shows the bearing component 2 and shim 4 coupled together within the knee joint. The joint may again be reduced and reassessed. It can be seen that the 6 mm markings 24 for the bearing component 2 visible in FIGS. 3A and 3B have been concealed and only the composite thickness markings 26 on the shim 4 are visible.

It will be appreciated that as a previous surgical step the size of the required tibial insert may already have been determined and so the initial insertion may be of the correct combination of the bearing component, plus shim if required, that is expected to provide the correct fit. The insertion of the composite trial prosthesis into the joint may effectively comprise only a confirmation that the previous identified size and shape of tibial insert is correct.

It will be appreciated that there may be a number of separate first components having different bearing surfaces (indicated by marking 20) but the same thickness (indicted by marking 24) corresponding to the minimum available thickness of tibial insert. Similarly, there may be a range of different thickness shims 4 indicated by markings 28 and arranged to couple to any of the first components 2. Alternatively, each shim may have the same thickness but the shims may have differing features to mimic different behaviour and properties of the tibial prostheses. For instance, a first shim may correspond to a rotating prosthesis and a second shim may correspond to a fixed prostheses, the first and second shims having the same upper surface for coupling to the reverse side of the bearing component but different lower surfaces for coupling to the trial tibial trays. The various shims may provide different centres of rotation, different angles of rotation axis, different widths and/or different depths.

It will be appreciated that in alternative embodiments only one recess and tab may be provided. As an alternative, the tabs 26 may be extended and arranged to obscure a greater amount of information in one or more extended recesses on the first component. A range of different thicknesses may be indicated in the recess and each shim may have a different length tab to selectively reveal only a single marking indicating the composite thickness. The tab may have a window to selectively reveal certain information printed in the recess, for instance the size and shape of the corresponding femoral prosthesis.

It will be appreciated that alternative embodiments of the present invention may relate to different forms of trial prostheses, for use in different parts of the knee joint or in different surgical procedures. At its most general the present invention relates to the selective display and concealment of information when different components of a trial prosthesis are coupled together.

It will be readily apparent to the appropriately skilled person that further modifications may be made to the present invention and further applications may be found for the present invention from the teaching herein, without departing from the scope of the appended claims.

The invention claimed is:

1. A composite trial prosthesis for attachment to a bone or a further prosthetic component, comprising:
   a first component having a first surface corresponding to a surface of a prosthetic component and a reverse surface, the reverse surface having a first marking arranged to be visible when the first component is coupled to the bone or the further prosthetic component; and
   a shim configured to be coupled to the reverse surface, the shim having a second marking, wherein, when the shim is coupled to the first component, a part of the shim obscures the first marking and the second marking is visible when the shim is coupled to the first component.

2. The composite trial prosthesis of claim 1, wherein the first marking is indicative of the thickness of the first component and the second marking is indicative of the thickness of the composite trial prosthesis or a property of shim.

3. The composite trial prosthesis of claim 1, wherein the shim further comprises a tab arranged to extend over the first component when the shim is coupled to the reverse surface of the first component to obscure the first marking.

4. The composite trial prosthesis of claim 3, wherein the first component has a recess and the first marking is at least partially located within the recess, and, when the shim and the first component are coupled to one another, the shim tab extends into the recess to obscure the first marking.

5. The composite trial prosthesis of claim 3, wherein the second marking is at least partially located on the tab.

6. The composite trial prosthesis of claim 3, wherein the tab further has a window that allows at least part of the first component to be visible through the window when the shim is coupled to the reverse surface of the first component.

7. The composite trial prosthesis of claim 3, wherein the shim comprises at least two tabs and the first component comprises at least two markings, each tab being arranged to obscure one of the at least two markings of the first component when the shim is coupled to the first component.

8. The composite trial prosthesis of claim 1, wherein the first surface comprises a bearing surface that corresponds to a bearing surface of the prosthetic component.

9. The composite trial prosthesis of claim 8, wherein the composite trial prosthesis comprises a trial tibial prosthesis and is arranged to couple to a trial tibial tray.

10. The composite trial prosthesis of claim 9, wherein the first and second markings are visible at one or more of an anterior-medial and an anterior-lateral position when the trial tibial prosthesis is inserted into a knee joint.

11. A set of composite trial prostheses, comprising:
    the composite trial prosthesis of claim 1; and
    at least one further shim arranged to couple to the reverse surface of the first component, wherein each of the at least one further shims has a different thickness compared with the shim and the other at least one further shims or a different shape compared with the shim and the other at least one further shims.

12. The set of composite trial prostheses of claim 11, further comprising at least one further first component arranged to couple to the shim and each of the at least one further shims, each of the at least one further first component having a first surface shape that is different than the first surface of the first component.

13. A method of assembling a composite trial prosthesis, comprising the steps of:
    coupling a reverse surface of a first component to a bone or a further prosthetic component, the first component having a first surface corresponding to a surface of a prosthetic component, and a marking that is visible when the first component is coupled to the bone or the further prosthetic component;
    coupling a shim between the reverse surface of the first component and the bone or the further prosthetic component, the shim having a second marking, the shim and first component configured such that the marking of the first component is covered by the shim and the second marking is visible when the shim is coupled between the reverse surface of the first component and the bone or the further prosthetic component.

14. A composite trial prosthesis for attachment to a bone or a further prosthetic component, comprising:
    a bearing component having a bearing surface sized and shape similarly to a surface of a prosthetic component and a reverse surface having a first marking arranged to be visible when the bearing component is attached to the bone or the further prosthetic component; and
    a shim configured to be coupled to the reverse surface having a second marking, wherein, when the shim is coupled to the bearing component, a part of the shim covers the first marking and the second marking is visible when the shim is coupled to the bearing component.

* * * * *